United States Patent [19]
Young et al.

[11] Patent Number: 5,891,149
[45] Date of Patent: *Apr. 6, 1999

[54] APPARATUS FOR REMOVAL OF PLASTICS CEMENT

[75] Inventors: Michael John Radley Young, Ashburton; Brian Robert Denis Peter Bradnock, Hemel Hempstead, both of United Kingdom

[73] Assignee: Orthosonics, Ltd., United Kingdom

[*] Notice: The term of this patent shall not extend beyond the expiration date of Pat. No. 5,536,266.

[21] Appl. No.: 882,873

[22] Filed: Jun. 26, 1997

Related U.S. Application Data

[63] Continuation-in-part of PCT/GB95/03053 Dec. 27, 1995.

[30] Foreign Application Priority Data

Dec. 30, 1994 [GB] United Kingdom .................... 9426397

[51] Int. Cl.⁶ .................................................. A61B 17/00
[52] U.S. Cl. ............................... 606/80; 606/27; 606/84; 606/92; 606/169
[58] Field of Search ................................. 606/80, 27, 84, 606/92, 169

[56] References Cited

U.S. PATENT DOCUMENTS 5,536,266    7/1996    Young et al. .............................. 606/27

Primary Examiner—Michael Buiz
Assistant Examiner—Lien Nao
Attorney, Agent, or Firm—Hopgood, Calimafde, Kalil & Judlowe

[57] ABSTRACT

The apparatus for removal of bone-cement comprises means to generate an ultrasonic signal and a tool element including an elongate stem (1) to transmit the signal to a distal end:. A plurality of spoke members (3), preferably four or eight, extend radially from adjacent the distal end to connect with an annular member (2) surrounding and spaced from the distal end. A plurality of openings (4) are each defined by the stem (1), the annular member (2) and two of the spokes (3). The annular member (2) is provided with a distally facing cutting edge. The spokes (3) are so configured as to transmit to and allow axial movement of the annular member (2) with respect to the stem (1), with an enhanced displacement relative to that of the stem (1).

17 Claims, 3 Drawing Sheets

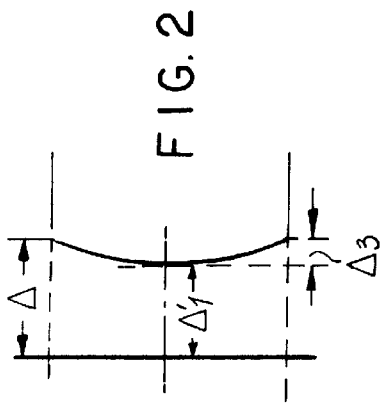
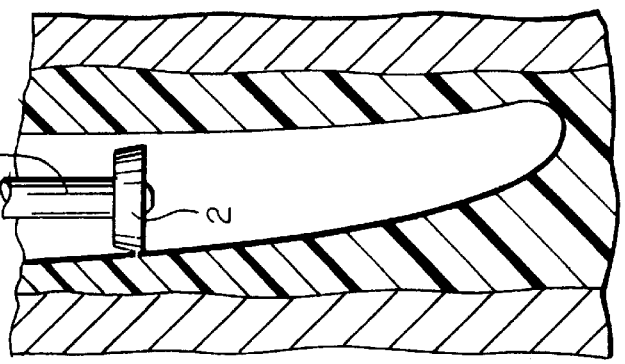
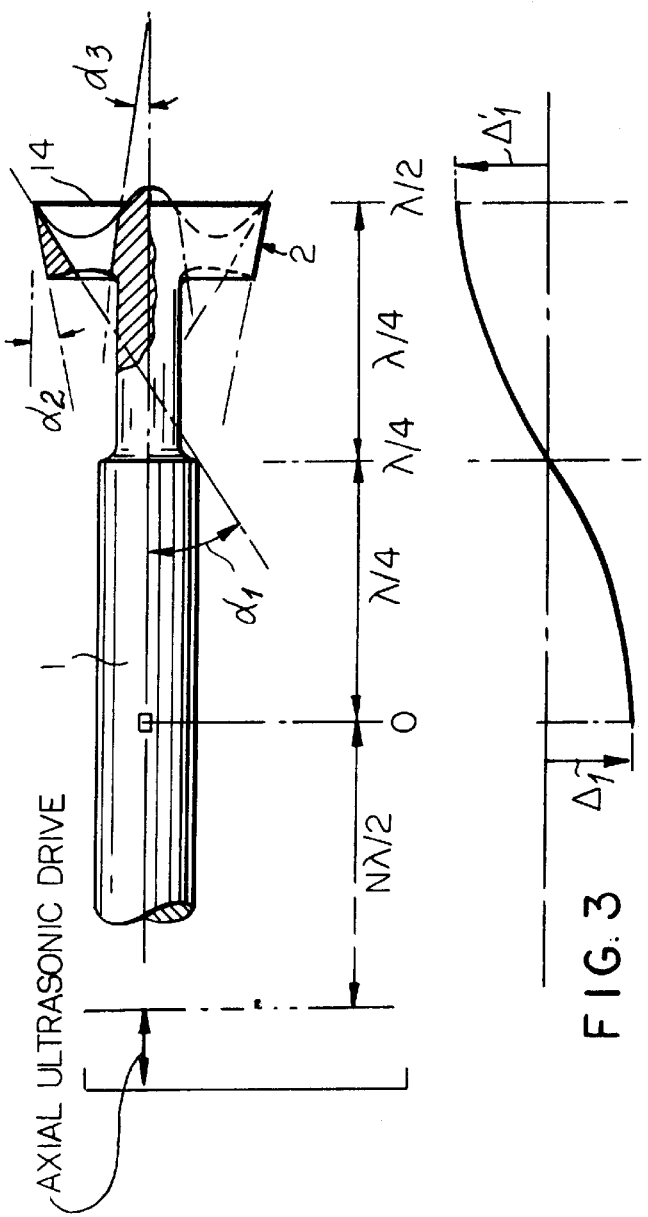

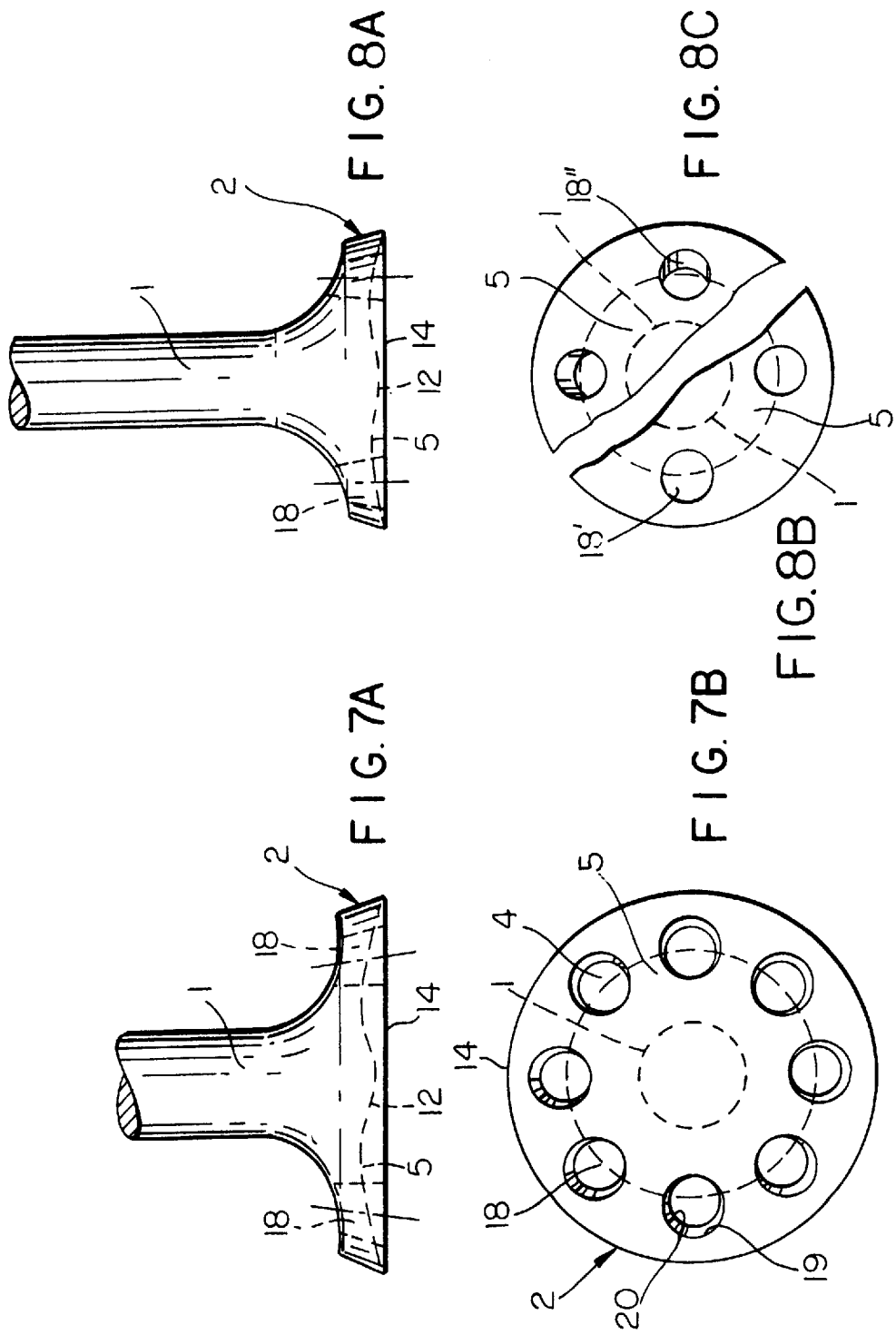

APPARATUS FOR REMOVAL OF PLASTICS CEMENT

RELATED CASE

This application is a continuation-in-part of pending application PCT/GB95/03053, filed 27 Dec. 1995.

FIELD OF INVENTION

The present invention relates to an improved apparatus for the removal of bone cement in the course of revision arthroplasty. More particularly, but not exclusively, it relates to removal of bone cement during a hip-joint prosthesis revision. Other joint-revision operations may also benefit from use of the apparatus, but for the sake of convenience, the following description will refer to hip-joint revisions, which term must be taken to include all other revision operations.

BACKGROUND OF THE INVENTION

It is known from our UK Patent No. 2229660B and our copending European patent Application No. 92917959.6 and from Engelbrecht U.S. Pat. No. 4,248,232 and Hood U.S. Des 341,202 that the local heating effect associated with the application of ultrasound to plastics materials can be employed to soften and effect the removal of bone cement during revision arthroplasty. Specifically, it has been shown in our previous patent and patent applications that a fundamental requirement of the cement removal technique is to influence the flow of softened material so that a small quantity of cement can be isolated and retained to be captured in the head of the activated instrument in order to extract it efficiently from the operating site, over a series of penetrating cycles. An important characteristic of such instruments is the presence of an axisymmetric disc close to the distal end of the instrument, and critically, of one or more connecting ports or passages parts between the distal face and an annular cavity proximal to said disc.

It is also known from our application No. EP 92917959.6 that the flow of softened cement is encouraged by the use of an annular cutting edge optionally incorporating a taper either towards or away from the distal end of the probe.

BRIEF STATEMENT OF THE INVENTION

It is an object of the invention to provide an ultrasonically driven apparatus of the character indicated with an improved tool-head construction for applying ultrasonic energy to the task of locally melting and removing plastics cementing material, as from a situs of cured prior installation of the plastics material.

Another object is to meet the above object and to improve the flow and control of softened plastics material, by incorporating axially compliant structure between axially resonant, integrally related component portions of the tool-head per se.

It is a further object of the invention to improve the proximally directional flow of distally softened plastics material by establishing a displacement gradient between an outer annular cutting edge and the longitudinal axis of the tool-head.

It is still another object to meet the above objects with an ultrasonically driven tool-head construction which will proximally pump softened plastics material in the course of distal advance of the toolhead into a body of plastics material to be removed.

According to a first aspect of the present invention there is provided an apparatus for removal of bone-cement comprising means to generate an ultrasonic signal, and elongate stem means to transmit said signal to a distal tool-head end thereof, wherein the tool-head end comprises an annular body portion having a distally facing cutting edge surrounding and radially spaced from a central-body portion at or near the distal end of the stem means, with an axially compliant perforate web integrally connected to and providing sole support of the outer-body portion with respect to the central-body portion, and wherein the web is perforate by reason of a distributed plurality of angularly spaced openings which establish communication passages between distally and proximally facing surfaces of the web, with web material of spoke-like configuration in the space between adjacent openings.

Preferably said stem means terminates distally as a substantially hemispherical or part-hemispherical working surface.

The angularly spaced openings and therefore the spoke-like configurations are advantageously disposed equiangularly around said stem means. In the case of four such openings, there are four spoke-like configurations; and present preference is for eight like openings, to thereby provide eight uniformly distributed spoke-like configurations which are integrally formed portions of the web, wherein the web itself is integrally formed with the annular outer-body portion and with the central-body portion at or near the distal end of the stem means.

The web may have a distally facing concave surface and may additionally or alternatively have a proximally facing concave surface.

The web may have an annular region of least axial thickness by reason of distally facing and/or proximally facing concavities, and the distributed openings may at least in part lap the annular region of least axial thickness.

The distal concavity may have an axial extent of up to one half of the axial extent of the outer annular body portion. And a proximal concavity may have an axial extent less than that of the distal cavity.

According to a second aspect of the present invention, there is provided tool means for use in the apparatus described above.

According to a third aspect of the present invention, there is provided a tool element for removal of bone-cementing plastics material, comprising an elongate shaft having a central axis and adapted for longitudinal transmission of ultrasonic energy from a proximal excitation end to a distal plastics-engaging end, said plastics-engaging end comprising a solid inner-body portion of substantially the diameter of said shaft and a solid annular outer-body portion radially offset from and in axial overlap with said inner-body portion, said outer-body portion extending between axially spaced circumferentially continuous distal and proximal limits, wherein the distal limit has a longitudinal section characterized by an acute angle which defines a circumferentially continuous distal cutting edge, and an angularly spaced plurality of radial members being of less axial extent than the axial extent of said outer-body portion and providing an axially compliant support of said outer body portion with respect to said inner-body portion.

Preferably, an axially compliant annular web is integrally formed with said inner-body portion and with said outer-body portion and provides the radial offset of said body portions from each other, said annular web having an angularly distributed plurality of axial passages which communicate between a distally facing web surface and a proximally facing web surface.

Advantageously, said distally facing web surface defines an annular distally open concavity. The axial depth of said distally open concavity may be substantially equal to or less than half the axial space between said limits. Also, advantageously, said proximally facing web surface may define an annular proximally open concavity within the region of radial offset of said outer-body portion from said inner-body portion. The axial depth of said proximally open concavity may advantageously be less than the axial depth of said distally open concavity.

The acute angle defining the distal cutting edge may be in the range of 15° to 25°.

The outer-body portion may have a frusto-conical outer surface which converges in the proximal direction and wherein said outer surface terminates distally at said distal cutting edge, and the convergence of said outer annular surface is in the range from substantially zero to 15 degrees with respect to said axis.

According to a fourth aspect of the present invention, there is provided an apparatus comprising a tool element as described in the third aspect above, in combination with piezo ceramic transducer means adapted to impart ultrasonic energy to said elongate shaft.

BRIEF DESCRIPTION OF THE DRAWINGS

Embodiments of the invention will now be more particularly described by way of example and with reference to the accompanying drawings, in which:

FIG. 1 shows schematically a tool head of an apparatus embodying the invention; the driven end of the stem of the tool-head being broken away to avoid unnecessary showing of its connection to ultrasonic means for longitudinal excitation of the tool via its stem;

FIG. 2 is a diagrammatic illustration showing flexural displacement amplitude across the tool head during use of the apparatus;

FIG. 3 is a diagrammatic illustration of a waveform showing longitudinal displacement amplitude along the stem and tool head of the apparatus;

FIG. 4 is a diagram to show use of the apparatus in removing bone cement from a revision cavity;

FIGS. 7A and 7B respectively show in side elevation and plan view a tool head having an axially compliant annular web with eight angularly distributed axial passages; and FIGS. 8A, 8B and 8C respectively, are similar to FIGS. 7A and 7B to similarly show a tool head with an axially compliant web having only four axial passages, but of individually modified specific nature.

Figure 6:
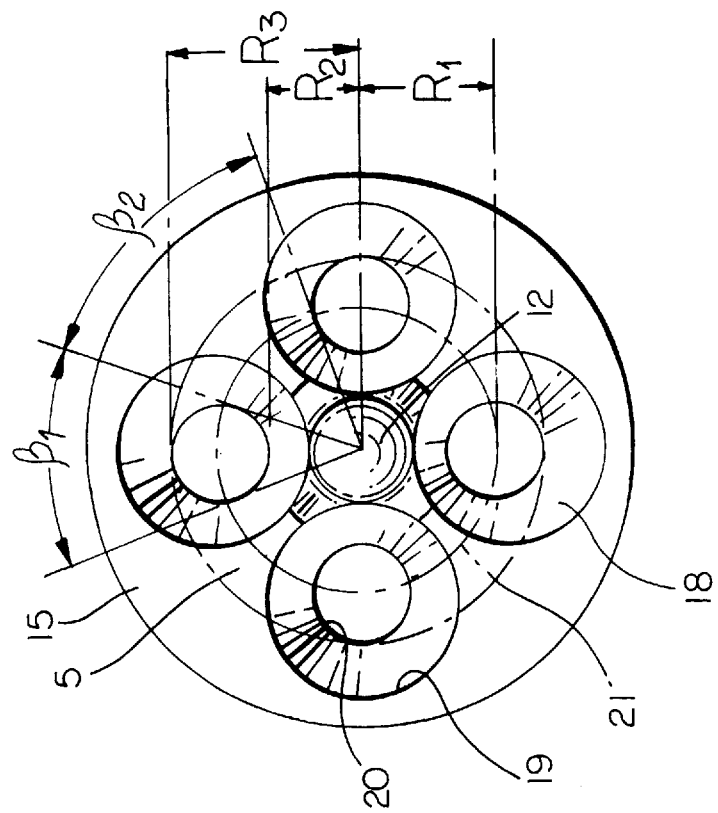
FIG. 6 is a front elevation of the distally facing end of the tool head of FIG. 5.

DETAILED DESCRIPTION.

Referring now to the drawings, FIG. 1 shows the tool head end of the apparatus, partially in cross section.

FIGS. 2 and 3 show respectively the waveforms, generated in use, across the working face of the tool head, and along the stem.

As is shown most clearly in FIGS. 1 and 3, ultrasonic energy suggested by legend as a double-headed arrow, is transmitted along a tool stem 1 and therethrough to an annular cutting ring 2, which is integrally formed with axially compliant radial-offset structure, to flex axially with respect to stem 1. The axial compliance enables the cutting ring 2 of the tool head to develop an oscillating axial displacement which exceeds that of the stem portion to which it is integrally united, thus occasioning a displacement gradient from the stem to the cutting ring.

Figure 5:
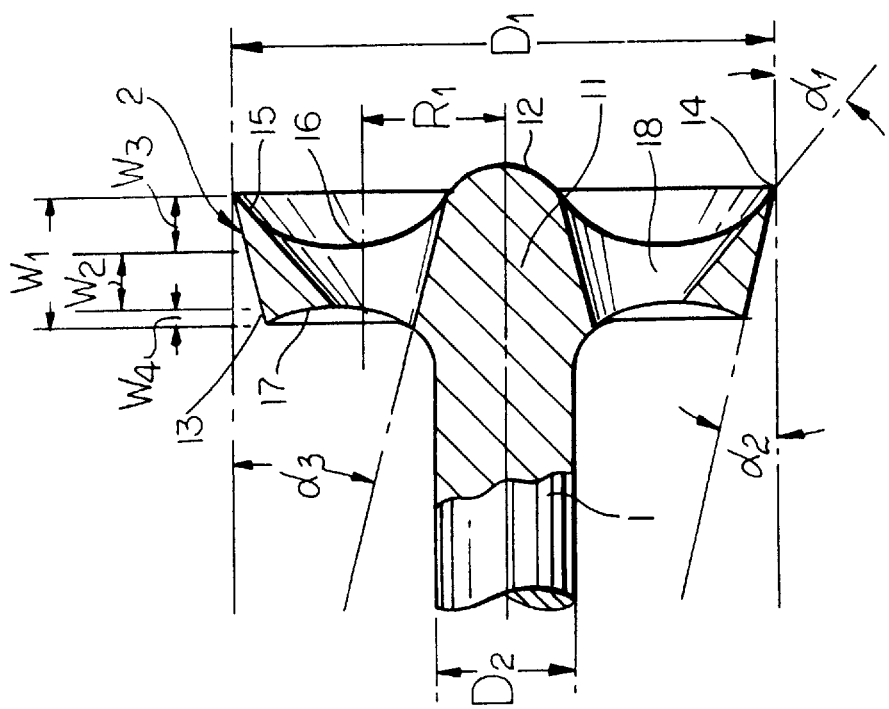
FIG. 5 is a longitudinal section to show in more detail the tool head of the invention.

More specifically and with additional reference to FIGS. 5 and 6, an axially compliant web 5 is the means of axially compliant support of cutting ring 2 at radial offset from the distal-end portion 11 of stem 1. The cutting ring 2 may be viewed as a relatively massive circumferentially continuous outer-body member, and the web 5 establishes integral connection of the outer-body member 2 to stem 1 at what may be viewed as a central-body member 11 at the distal end of stem 1, being shown to terminate distally in a convex generally spherical end contour 12, centered on axis 12 of the tool head.

The outer-body member 2 is shown with a frustoconical outer surface 13 which converges in the proximal direction from a distal limit of maximum tool-head diameter D at which a relatively sharp circumferentially continuous cutting edge 14 is derived from intersection of surface 13 with a circumferentially continuous concave frustoconical inner surface 15. The concave surface 15 defines the outer annular region of a characterising annular concavity 16 which is distally open and which is shown to fair continuously with the blunt convex central distal-end profile 12 of the inner or central body member 11. The sectional slope of concave surface 15 is identified $\alpha_1$ with respect to the central axis of the tool head, and the slope of the outer convex surface 13 is identified $\alpha_2$, also with respect to the central axis.

Another annular concavity feature 17 of outer-body member 2 and of web 5 is proximally open, being shown to extend from the proximal-end limit of member 2, in radial offset from the inner-body portion 11 of the stem. Dimensional symbol $W_1$ FIG. 5 designates the overall axial extent of outer-body member 2, and $W_2$ designates the minimum axial extent of web 5, by reason of a greater axial depth $W_3$ of concavity 16 as compared to a lesser axial depth $W_4$ of concavity 17, a preference being indicated for a greater depth $W_3$ of the distal face of web 5 than for the depth $W_4$ of the proximal face of web 5. And the axially narrow annular web region between concavities 16, 17 is relied upon for axial compliance in the support of the outer-body member 2 (and its cutting edge 14) with respect to the inner (central) body member 11. Suitably and preferably the axial depth $W_3$ is in the order of half the overall outer-body width $W_1$, and the axial depth $W_4$ is at most in the order of one half the axial depth $W_3$.

It is a feature of the invention that plural angularly spaced longitudinal openings or passages 18 be provided in the compliant web formation 5, in at least radial overlap with the web region of minimum axial thickness $W_2$. As shown in FIGS. 1, 5 and 6, these passages are generally frustoconical, convergent in the proximal direction (i) from an outer maximum sectional slope $\alpha_1$, of substantial tangency to the annular concave surface which intersects convex surface 13 to form the cutting edge 14, and (ii) to an inner minimum sectional slope $\alpha_3$ at the inner limit of the distally facing concavity 16, it being understood that the inner minimum sectional slopes $\alpha_3$ may range from zero to substantially 20 degrees, depending upon the extent to which the radially inner limit of web concavity 16 may have invaded the distal end stem portion 11 at less than the diameter D of stem 1.

With apologies for the schematic showings in FIGS. 5 and 6, each of the passages 18 will be seen in FIG. 6 to extend from a larger diameter generally circular distal entrance 19 to a lesser-diameter generally circular proximal exit 20, wherein the circular locus 21 of centers of passage exits 20 from web 5 is at a reduced radius $R_1$, that is radially inwardly offset from the center at which each circular entrance 19 is determined, thus accounting for a preferred inwardly sloped frustoconical axis for, each proximally convergent opening. Legends in FIG. 6 also identify an effective angular width $\beta_1$ at each passage exit 20 and an effective angular spacing $\beta_2$ between adjacent passage exits 20. Further legends identify, with respect to the central axis of the tool head, the minimum radius $R_2$ of each passage exit 20 and the maximum radius $R_3$ of each passage exit 20; and it is apparent from FIG.6 that each passage entrance 19 is at or near adjacency to its respective adjacent passage entrances 19.

A preference is indicated that the described tool-head and its stem 1 be integrally formed as a single tool bit, of a titanium-based alloy with vanadium and aluminium, suitably titanium alloyed with substantially 6 percent vanadium and substantially 4 percent aluminium.

Upon ultrasonic longitudinal excitation of the described tool bit, FIG.3 will be seen to illustrate a standing-wave situation to the longitudinal scale of FIG.1, and in reference to an antinodal point "0" which will be understood to have an integer-multiple half-wave relation ($N\lambda/2$) to the source of ultrasonic-drive excitation; and two successive $\lambda/4$ relations are labeled from the antinodal point to the distal end 12 of the stem portion 11 of the tool head. Observing distally from the antinodal point "0", a negative maximum of amplitude $\Delta_1$ is seen to reduce in sinusoidal fashion to polarity crossover at stem 1 step-down to a reduced diameter, which will be understood to be the dimension $D_2$ of FIG. 5, thus accounting for what will be understood to be an increased magnitude $\Delta'_1$ at the distal end of stem portion 11, the next antinodal point.

The diagram of FIG. 2 illustrates longitudinal displacement amplitude as a function of radius about the central axis of the tool, reflecting increased displacement amplitude observed at the cutting edge (distal outer limit) 14, by reason of the compliant integral web (5) connection between inner body (11) and outer-body (2) masses of the tool bit. In FIG. 2, the amplitude $\Delta'_1$ has been labeled as have also the enlarged amplitude levels $\Delta_2$ at diametrically opposite parts of the sectional sense of FIG. 2, which will be understood to apply with substantial uniformity over the circumferential continuity of cutting edge 14. Specifically in FIG. 2, the dimensional quantity $\Delta_3$ will be understood to express the incrementally increased amplitude of resonantly excited action by reason of the compliant web-coupled connection to outer annular member 2 and its cutting edge.

It is to be noted that by having reduced the axial projection of the distal end of the tool bit, from the bore centering additional length shown in our U.S. Pat. No. 5,536,266 to virtual coincidence with the transverse plane which contains cutting edge 14, it has become possible to establish a distal antinodal point substantially at the plane of cutting edge 14, thus enhancing the compliant flexural displacement gradient associated with the compressional standing wave of FIG.3, and thus also enhancing the effectiveness of the peripheral cutting edge 14.

FIG.4 illustrates relevance of the described structural relationship when in longitudinally driven ultrasonic resonance, specifically in application to enlargement and penetration of the distal cemented region which remains after extraction of an appliance such as the femoral component of a hip-joint implant. Such extraction leaves a curved horn-shaped cavity in the bone cement, a plastics material which for a hip-joint replacement requires volume enlargement in order to assure correct replacement setting in fresh cement to complete a replacement procedure. In FIG. 4, the cutting edge 14 is shown with circumferentially arcuate engagement to a portion of the cavity in the older plastics cement, enabling the operation to selectively shave local regions of the cavity wall, to enlarge and shape the cavity for correct acceptance of the new prosthetic appliance with fresh cement. Such edgewise wall contact and shaving action will permit acceptance of a new prosthetic wall contour, and the depth of oldplastics penetration and removal can also be enlarged without need for tool contact with bone.

In the foregoing, the axially compliant web 5 has been described as perforate, by reason of the angularly spaced passages or openings 18. From another aspect,the web material between adjacent openings 18 may be viewed as generally radial spokes or as generally spoke-like, wherein the mean circumferentially arcuate width of each spoke is $\pi R_1/n$ in the event of $\beta_1=\beta_2$ and $\beta_1+\beta_2=2\pi/n$ where is the number of equally spaced passages 18.

Use of apparatus according to above-indicated dimensions and axially compliant relationships has shown a freer flow of plastics cement material through the openings of passages 18 and, therefore, an improved rate of proximally expelled plastics material that has been removed from the region of distally softened material. Not only is the proximally directed flow at an improved rate, but such flow amounts to a pumping action, in that proximally directed flow is observed to occur against the action of gravitational forces.

The embodiment of FIG.7 illustrates a form of the invention which has a compliant web 5 with eight equally spaced proximally convergent frustoconical passages 18, wherein the cutting diameter at 14 is 11.8 mm, and wherein each passage is of 1.5 mm diameter. This configuration has been measured to exhibit an axially vibrational amplitude of $51\pm2.5$ $\mu$m at the center of end surface 12, while exhibiting an axially vibrational cutting surface (14) amplitude of $74\pm4$ $\mu$m.

More specifically as to FIG. 7, the eight frustoconical passages 18 are seen to be on proximally inwardly directed axes, by reason of greater diameter entrance edges 19 that are on axially projected alignment with lesser diameter exit edges 20 which are in tangential register at their minimum radial offset from the central axis of the tool bit.

FIG. 8A is illustrative of a four-passage tool bit wherein the passages 18 are again frustoconical but on an axis which is substantially parallel to the central axis of the structure. In this embodiment, which has been the subject of clinical testing, the cutting diameter was 9.29 mm and stem diameter was 5.05 mm, thus exemplifying a diameter ratio of 1.84. In the clinical tests with ultrasonic excitation in the range 28.1 to 28.5 kHz, cement-cutting performance was rated highly efficient in terms of volumetric removal, high mechanical stability, and ability to stay in tune, (i.e. locked in standing-wave resonance), all without exhibiting mechanical failure, despite repeated sterilization between multiple surgeries. Additionally, the cutting action was selflimiting on plastics cement, to the exclusion of invading bone, i.e. there was no evidence of cutting bone tissue.

FIGS. 8B and 8C are different fragmentary end views of the configuration of FIG.8A, except for the fact that in FIG. 8B, each of the passages 18 is a straight cylindrical bore generally parallel to the tool-bit axis; whereas in FIG. 8C, each of the passages 18 is a straight cylindrical bore, on an axis convergent proximally toward the central axis of the tool bit, with proximal exit alongside the stem 1, the diameter of which is suggested in FIGS. 8B and 8C, by dashed semi-circular arcs.

It is preferred that the ratio between the diameters of the tool head and of the stem shall be in the range between 1.75:1 and 2.25:1.

It will be seen that the described invention meets all stated objects and achieves, through the indicated integrally formed axially compliant coupling of inner and outer body members a greatly enhanced plastics-removal effectiveness. The flow of plastics cement material is so enhanced that the material will not only pass more easily through the passages 18, but will also be encouraged to pass up the stem 1, possibly as far as the first nodal point. And because the plastics removal is more rapid and effective than heretofore, as well as being relatively harmless to bone tissue, the invention achieves improved safety for the patient.

What is claimed is:

1. A one-piece tool element of elastic material for removal of bone-cementing plastics material, comprising an axially elongate shaft adapted for longitudinal transmission of ultrasonic energy from a proximal excitation end to a distal plastics-engaging end, said plastics-engaging end comprising an annular body having a circumferentially continuous outer-body mass and an annular web integrally and axially compliantly connecting said outer-body mass to said shaft, said outer-body mass being defined by and between an axially spaced distal limit and a proximally spaced proximal limit, such that in a longitudinal section an acute angle is defined by a distally directed circumferentially continuous distal cutting edge, said annular web having a minimum axial thickness which is less than the axial distance between said distal limit and said proximal limit, and said annular web being at axially inward offset from the distal limit of said annular body such that a distally open annular concavity is defined adjacent said distal cutting edge and within said outer-body mass, with angularly spaced longitudinal passages in an annular region of said web and thus in the region of said annular concavity for flowing distally melted plastics material via said passages from said annular concavity and to the proximal side of said annular body.

2. The tool element of claim 1, in which said annular concavity is proximally convergent with respect to said shaft, from said cutting edge to the annular region of said passages.

3. The tool element of claim 2, in which said annular body has a circumferentially continuous outer surface and in which said distal and proximal limits are axial limits of said outer surface.

4. The tool element of claim 1, in which said passages are cylindrical.

5. The tool element of claim 1, in which said passages are generally frustoconical and convergent in the proximal direction.

6. The tool element of claim 4, in which the axes of said passaged are convergent in the proximal direction.

7. The tool element of claim 5, in which each frustoconical passage is about an axis which is convergent with respect to and in the proximal direction of said axially elongate shaft.

8. The tool element of claim 3, in which said circumferentially continuous outer surface is frustoconically convergent in the proximal direction.

9. A one-piece tool element of elastic material for proximally pumped removal of bone-cementing plastics material, that is softened by ultrasonically excited, comprising an elongate shaft adapted for longitudinal transmission of ultrasonic energy from a proximal excitation end to a distal plastics-engaging end, said plastics-engaging end comprising an annular body having a circumferentially continuous outer-body mass and an annular web integrally and axially compliantly connecting said outer-body mass to said shaft, said outer-body mass being defined by and between an axially spaced distal limit and an axially spaced proximal limit, said annular web being at axially inward offset from the distal limit of said annular body such that a distally open annular concavity is defined within said outer-body mass, with angularly spaced longitudinal passages in an annular region of said web and thus in the region of said annular concavity, for flowing distally melted plastics material via said passages from said annular concavity and to the proximal side of said annular body.

10. The tool element of claim 9, in which said annular concavity has in a longitudinal section a distally open arcuate concave profile.

11. The tool element of claim 9, in which said longitudinal passages are at least in part in the region of axially compliant web connection to said shaft.

12. The tool element of claim 9, in which a distally convex central end formation of said shaft essentially defines with the distal limit of said outer-body mass the distal limit of said tool element.

13. The tool element of claim 9, in which said annular body has a proximally open annular concavity at least in part within said outer-body mass.

14. A one-piece tool element for removal of bone-cementing plastics material, comprising an elongate shaft adapted for longitudinal transmission of ultrasonic energy from a proximal excitation end to a distal plastics-engaging end, said plastics-engaging end comprising an annular body having a circumferentially continuous outer surface of diameter exceeding that of said shaft and integrally formed with said shaft, said annular body being defined by and between an axially spaced distal limit and a proximally spaced proximal limit, such that the distal limit has in a longitudinal section an acute angle defined by a distally directed circumferentially continuous distal cutting edge, and a distally convex central end formation of said shaft substantially defining with said distal cutting edge the distal end of said tool element, said distally convex central end formation of said shaft extending from a base end that is axially between the proximal and distal limits of said annular body and at radially inward offset from the outer surface of said annular body such that a distally open annular concavity is defined adjacent said distal cutting edge and within said annular body, with angularly spaced longitudinal passages in the region of said annular concavity, for flowing distally melted plastics material via said passages from said annular concavity and to the proximal side of said annular body, the axial thickness of said annular body being at minimum in the annular region of said longitudinal passages, thereby establishing an outer annular body mass radially outside said annular region such that said annular region defines an axially compliant integral connection between said shaft and said outer annular body mass.

15. The tool element of claim 14, in which the distal end of said distally convex central end formation and the distal limit of said annular body are in substantially the same radial plane.

16. The tool element of claim 14, in which the distal end of said distally convex central end formation is axially within said annular body.

17. The tool element of claim 14, in which the distal end of said distally convex central end formation projects at least in part distally beyond the distal limit of said annular body.

* * * * *